United States Patent [19]

Miyazaki et al.

[11] Patent Number: 5,789,380
[45] Date of Patent: Aug. 4, 1998

[54] AGENTS FOR INHIBITING ACCUMULATION OF VISCERAL FAT

[75] Inventors: Toshiyuki Miyazaki; Toshihisa Morimoto, both of Saitama-ken; Ryuji Murayama, Hyogo-ken; Sachiko Takase, Shizuoka; Toshinao Goda, Shimizu, all of Japan

[73] Assignees: Nisshin Flour Milling Co., Ltd., Tokyo; Nagata Sangyo Co., Ltd., Hyogo-ken, both of Japan

[21] Appl. No.: 782,177

[22] Filed: Jan. 14, 1997

[30] Foreign Application Priority Data

Jan. 18, 1996 [JP] Japan .................................. 8-023445

[51] Int. Cl.$^6$ ............................ A61K 38/16; C07K 14/00
[52] U.S. Cl. .................................................. 514/12; 530/350
[58] Field of Search ............................. 514/12; 530/350; 435/201

[56] References Cited

U.S. PATENT DOCUMENTS

| 5,332,803 | 7/1994 | Miyazaki et al. . |
| 5,440,019 | 8/1995 | Miyazaki et al. . |
| 5,444,046 | 8/1995 | Miyazaki et al. . |

FOREIGN PATENT DOCUMENTS

| 618299 | 10/1994 | European Pat. Off. . |
| 5-301898 | 11/1993 | Japan . |
| 7-41499 | 2/1995 | Japan . |
| 7-48268 | 2/1995 | Japan . |
| 7-48400 | 2/1995 | Japan . |

OTHER PUBLICATIONS

Koji Maeda, et al. "Complete Amino Acid Sequence of an Alpha-Amylase Inhibitor in Wheat Kernel 0.19-Inhibitor", Biochimica Et Biophysica Acta, vol. 828, (pp. 213–221), 1985.

K. Maeda, et al. "Complete Amino Acid Sequence of an Alpha-Amylase Inhibitor in Wheat Kernel", Biochimica Et Biophysica Acta, vol. 743, (pp. 52–57), 1983.

Nizar Kashlan, et al. "The Complete Amino Acid Sequence of a Major Wheat Protein Inhibitor of Alpha-Amylase", Phytochemistry, vol. 20, No. 8, (pp. 1781–1784), 1981.

Yasutoshi Muto, et al. "Selective Dampening of Lipogenic Enzymes of Liver By Exogenous Polyunsaturated Fatty Acids", Biochemical and Biophysical Research Communications, vol. 38, (pp. 9–15), 1970.

*Primary Examiner*—Charles L. Patterson, Jr.
*Attorney, Agent, or Firm*—Oblon, Spivak, McClelland, Maier & Neustadt, P.C.

[57] ABSTRACT

An agent for inhibiting an accumulation of visceral fat is disclosed which comprises an amylase inhibitor of wheat origin as an active ingredient. The agent is effective for inhibiting the accumulation of visceral fat in the viscus, thus preventing the visceral fat obesity which may be one of the causes of adult diseases.

6 Claims, 1 Drawing Sheet

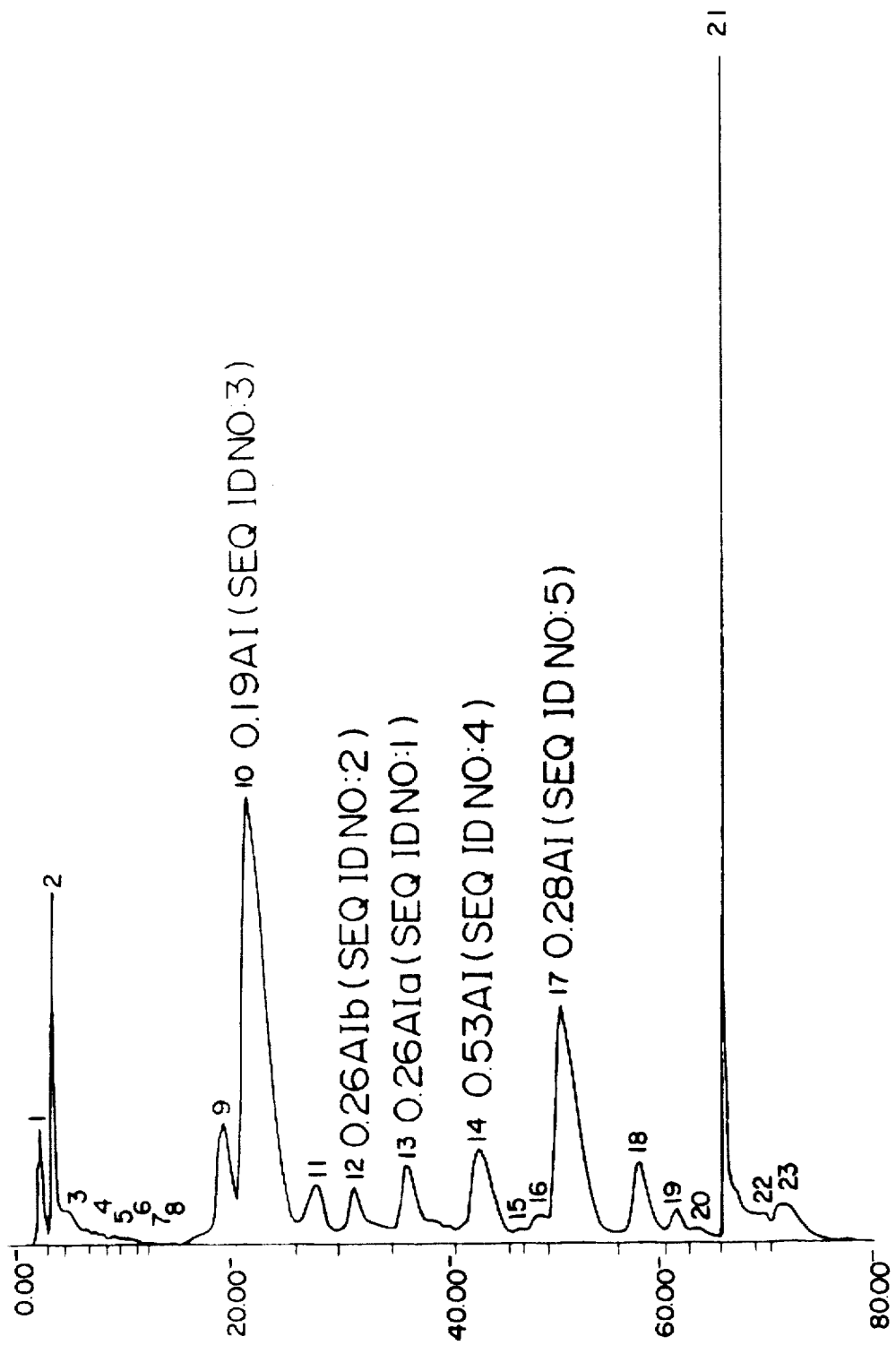

SEQUENCE LISTING ( 1 ) GENERAL INFORMATION:

( i i i ) NUMBER OF SEQUENCES: 5

( 2 ) INFORMATION FOR SEQ ID NO:1:

( i ) SEQUENCE CHARACTERISTICS:
        ( A ) LENGTH: 124 amino acids
        ( B ) TYPE: amino acid
        ( C ) STRANDEDNESS: single
        ( D ) TOPOLOGY: linear ( i i ) MOLECULE TYPE: protein ( x i ) SEQUENCE DESCRIPTION: SEQ ID NO:1:

```
Ser Gly Pro Trp Met Cys Tyr Pro Gly Tyr Ala Phe Lys Val Pro Ala
  1               5                  10                  15
Leu Pro Gly Cys Arg Pro Val Leu Lys Leu Gln Cys Asn Gly Ser Gln
             20                  25                  30
Val Pro Glu Ala Val Leu Arg Asp Cys Cys Gln Gln Leu Ala Asp Ile
         35                  40                  45
Ser Glu Trp Cys Arg Cys Gly Ala Leu Tyr Ser Met Leu Asp Ser Met
     50                  55                  60
Tyr Lys Glu His Gly Val Gln Glu Gly Gln Ala Gly Thr Gly Ala Phe
 65                  70                  75                  80
Pro Ser Cys Arg Arg Glu Val Val Lys Leu Thr Ala Ala Ser Ile Thr
                 85                  90                  95
Ala Val Cys Lys Leu Pro Ile Val Ile Asp Ala Ser Gly Asp Gly Ala
            100                 105                 110
Tyr Val Cys Lys Gly Val Ala Ala Tyr Pro Asp Ala
            115                 120
```

( 2 ) INFORMATION FOR SEQ ID NO:2:

( i ) SEQUENCE CHARACTERISTICS:
        ( A ) LENGTH: 122 amino acids (B) TYPE: amino acid
(C) STRANDEDNESS: single
(D) TOPOLOGY: linear (ii) MOLECULE TYPE: protein (xi) SEQUENCE DESCRIPTION: SEQ ID NO:2:

| Ser | Gly | Pro | Trp | Met | Cys | Tyr | Pro | Gly | Tyr | Ala | Phe | Lys | Val | Pro | Ala |
|---|---|---|---|---|---|---|---|---|---|---|---|---|---|---|---|
| 1 | | | | 5 | | | | | 10 | | | | | 15 | |
| Leu | Pro | Gly | Cys | Arg | Pro | Val | Leu | Lys | Leu | Gln | Cys | Asn | Gly | Ser | Gln |
| | | | 20 | | | | | 25 | | | | | 30 | | |
| Val | Pro | Glu | Ala | Val | Leu | Arg | Asp | Cys | Cys | Gln | Gln | Leu | Ala | Asp | Ile |
| | | | 35 | | | | 40 | | | | | 45 | | | |
| Ser | Glu | Trp | Cys | Arg | Cys | Gly | Ala | Leu | Tyr | Ser | Met | Leu | Asp | Ser | Met |
| | 50 | | | | | 55 | | | | | 60 | | | | |
| Tyr | Lys | Glu | His | Gly | Val | Gln | Glu | Gly | Gln | Ala | Gly | Thr | Gly | Ala | Phe |
| 65 | | | | | 70 | | | | | 75 | | | | | 80 |
| Pro | Ser | Cys | Arg | Arg | Glu | Val | Val | Lys | Leu | Thr | Ala | Ala | Ser | Ile | Thr |
| | | | | 85 | | | | | 90 | | | | | 95 | |
| Ala | Val | Cys | Lys | Leu | Pro | Ile | Val | Ile | Asp | Ala | Ser | Gly | Asp | Gly | Ala |
| | | | | 100 | | | | | 105 | | | | | 110 | |
| Tyr | Val | Cys | Lys | Gly | Val | Ala | Ala | Tyr | Pro | | | | | | |
| | | | 115 | | | | | 120 | | | | | | | |

(2) INFORMATION FOR SEQ ID NO:3:

(i) SEQUENCE CHARACTERISTICS:
(A) LENGTH: 124 amino acids
(B) TYPE: amino acid
(C) STRANDEDNESS: single
(D) TOPOLOGY: linear (ii) MOLECULE TYPE: protein (xi) SEQUENCE DESCRIPTION: SEQ ID NO:3:

| Ser | Gly | Pro | Trp | Met | Cys | Tyr | Pro | Gly | Gln | Ala | Phe | Gln | Val | Pro | Ala |
|---|---|---|---|---|---|---|---|---|---|---|---|---|---|---|---|
| 1 | | | | 5 | | | | | 10 | | | | | 15 | |
| Leu | Pro | Ala | Cys | Arg | Pro | Leu | Leu | Arg | Leu | Gln | Cys | Asn | Gly | Ser | Gln |
| | | | 20 | | | | | 25 | | | | | 30 | | |
| Val | Pro | Glu | Ala | Val | Leu | Arg | Asp | Cys | Cys | Gln | Gln | Leu | Ala | His | Ile |
| | | | 35 | | | | 40 | | | | | 45 | | | |
| Ser | Glu | Trp | Cys | Arg | Cys | Gly | Ala | Leu | Tyr | Ser | Met | Leu | Asp | Ser | Met |
| | 50 | | | | | 55 | | | | | 60 | | | | |
| Tyr | Lys | Glu | His | Gly | Ala | Gln | Glu | Gly | Gln | Ala | Gly | Thr | Gly | Ala | Phe |
| 65 | | | | | 70 | | | | | 75 | | | | | 80 |
| Pro | Arg | Cys | Arg | Arg | Glu | Val | Val | Lys | Leu | Thr | Ala | Ala | Ser | Ile | Thr |
| | | | | 85 | | | | | 90 | | | | | 95 | |
| Ala | Val | Cys | Arg | Leu | Pro | Ile | Val | Val | Asp | Ala | Ser | Gly | Asp | Gly | Ala |
| | | | | 100 | | | | | 105 | | | | | 110 | |
| Tyr | Val | Cys | Lys | Asp | Val | Ala | Ala | Tyr | Pro | Asp | Ala | | | | |
| | | | 115 | | | | | 120 | | | | | | | |

(2) INFORMATION FOR SEQ ID NO:4:

(i) SEQUENCE CHARACTERISTICS:
(A) LENGTH: 124 amino acids
(B) TYPE: amino acid
(C) STRANDEDNESS: single
(D) TOPOLOGY: linear (ii) MOLECULE TYPE: protein (xi) SEQUENCE DESCRIPTION: SEQ ID NO:4:

```
Ser Gly Pro Trp Met Cys Tyr Pro Gly Gln Ala Phe Gln Val Pro Ala
 1               5                  10                     15

Leu Pro Gly Cys Arg Pro Leu Leu Lys Leu Gln Cys Asn Gly Ser Gln
            20                  25                  30

Val Pro Glu Ala Val Leu Arg Asp Cys Cys Gln Gln Leu Ala Asp Ile
        35                  40                      45

Ser Glu Trp Pro Arg Cys Gly Ala Leu Tyr Ser Met Leu Asp Ser Met
    50                  55              60

Tyr Lys Glu His Gly Val Ser Glu Gly Gln Ala Gly Thr Gly Ala Phe
 65              70                      75                  80

Pro Ser Cys Arg Arg Glu Val Val Lys Leu Thr Ala Ala Ser Ile Thr
                85                  90                      95

Ala Val Cys Arg Leu Pro Ile Val Val Asp Ala Ser Gly Asp Gly Ala
            100                 105                 110

Tyr Val Cys Lys Asp Val Ala Ala Tyr Pro Asp Ala
            115             120
```

(2) INFORMATION FOR SEQ ID NO:5:

(i) SEQUENCE CHARACTERISTICS:
  (A) LENGTH: 123 amino acids
  (B) TYPE: amino acid
  (C) STRANDEDNESS: single
  (D) TOPOLOGY: linear (ii) MOLECULE TYPE: protein (xi) SEQUENCE DESCRIPTION: SEQ ID NO:5:

```
Ser Gly Pro Trp Ser Trp Cys Asn Pro Ala Thr Gly Tyr Lys Val Ser
 1               5                  10                     15

Ala Leu Thr Gly Cys Arg Ala Met Val Lys Leu Gln Cys Val Gly Ser
            20                  25                  30

Gln Val Pro Glu Ala Val Leu Arg Asp Cys Cys Gln Gln Leu Ala Asp
        35                  40                      45

Ile Asn Asn Glu Trp Cys Arg Cys Gly Asp Leu Ser Ser Met Leu Arg
    50                  55              60

Ala Val Thr Gln Glu Leu Gly Val Arg Glu Gly Lys Glu Val Leu Pro
 65              70                      75                  80

Gly Cys Arg Lys Glu Val Met Lys Leu Thr Ala Ala Ser Val Pro Glu
                85                  90                      95

Val Cys Lys Val Pro Ile Pro Asn Pro Ser Gly Asp Arg Ala Gly Val
            100                 105                 110

Cys Tyr Gly Asp Trp Cys Ala Tyr Pro Asp Val
            115             120
```

AGENTS FOR INHIBITING ACCUMULATION OF VISCERAL FAT

FIELD OF THE INVENTION

This invention relates to an agent for inhibiting an accumulation of visceral fat. More particularly, it is concerned with an agent for inhibiting the accumulation of visceral fat which comprises as an active ingredient an amylase inhibitor of wheat origin. Accumulation of visceral fat can be inhibited by the ingestion of the present agent to prevent a visceral fat obesity, which has been said to be one of the causes of adult diseases.

BACKGROUND OF THE INVENTION

Recently, people's plentiful diet results in the increase in adult diseases such as arteriosclerosis and diabetes. This is due to the obesity caused by excess ingestion of fats and carbohydrates, regardless of a reduced energy consumption by basal metabolism by aging, with a deficient exercise. In this connection, a visceral fat obesity with an accumulation of fat in the viscus has higher risk of causing an adult disease as compared with a subcutaneous fat obesity with an accumulation of fat in the subcutaneousness. In such situation, it is important to prevent the visceral fat obesity for prophylaxis of the adult diseases. Thus, it has been required to develop a substance or agent which can conveniently inhibit the accumulation of visceral fat. However, this has not been achieved.

An amylase inhibitor of wheat origin is known to inhibit the activity of human pancreatic α-amylase and moderate the digestion of the starch ingested, thus inhibiting an increase in blood glucose level and reducing an insulin secretion, so that the amylase inhibitor is effective for people having a high blood glucose level or a candidate for diabetes. It is also known that the amylase inhibitor of wheat origin is effective in weight control.

Under these circumstances, we have made extensive studies on the function and chemical structure of the amylase inhibitors of wheat origin and found an industrially efficient process for the preparation of amylase inhibitors having a high amylase inhibitory activity from the extract of wheat flour or the like. This process is disclosed in Japanese Patent Kokai 5-301898, 7-48268 and 7-48400. Then, we have found a novel protein composed of two subunits, each identified as SEQ ID No. 1, and having a very high activity, which is disclosed in Japanese Patent Kokai 7-41499.

BRIEF DESCRIPTION OF THE DRAWING

FIG. 1 is a chromatogram showing the peaks of the fractions obtained in Reference Example 1.

DETAILED DESCRIPTION OF THE INVENTION

We have continued further studies on the basis of our previous studies as explained above, and found that amylase inhibitors of wheat origin are effective for inhibiting the accumulation of visceral fat, thus leading to present invention. This finding is based upon the quite unexpected function of a different nature from those functions of the amylase inhibitors of wheat origin known hitherto, i.e., the functions to inhibit the digestion of a starch, an increase in blood glucose level and an insulin secretion and the function of a weight control.

Thus, the present invention provides an agent for inhibiting an accumulation of visceral fat which comprises as an active ingredient an amylase inhibitor of wheat origin.

The amylase inhibitors which can be used as an active ingredient in the agent of the present invention are not limited to specified ones, so far as they are of wheat origin and have a high amylase inhibitory activity.

The amylase inhibitors of wheat origin can include a known protein composed of two subunits, each identified as SEQ ID NO:1 (hereinafter referred to as "0.26 AIa")(see, Japanese Patent Kokai 7-41499); a new protein composed of two subunits, each identified as SEQ ID NO:2 (hereinafter referred to as "0.26 AIb"); a known protein composed of two subunits, each identified as SEQ ID NO:3 (hereinafter referred to as "0.19 AI")[see, Biochim. Biophys. Acta, Vol. 828, pp. 213–221 (1985), Japanese Patent Kokai 5-301898, Japanese Patent Kokai 7-48268]; a known protein composed of two subunits, each identified as SEQ ID NO:4 (hereinafter referred to as "0.53 AI")(see, Biochim. Biophys. Acta, Vol. 743, pp. 52–57 (1983)]; and a known protein identified as SEQ ID NO:5 (hereinafter referred to as "0.28 AI")(see, Phytochemistry, Vol. 20, No. 8, pp. 1781–1784 (1981)]. All of these proteins have an amylase inhibitory activity, but the proteins 0.26 AIa, 0.26 AIb and 0.19 AI have a higher amylase inhibitory activity as shown in the following Table 1. Accordingly, it is preferable that the agents for inhibiting the accumulation of visceral fat comprise as an active ingredient at least one of the amylase inhibitors 0.26 AIa, 0.26 AIb and 0.19 AI, which have a higher amylase inhibitory activity.

TABLE 1

| Type of protein of wheat origin | | Amylase inhibitory activity (U/mg) |
|---|---|---|
| 0.26 AIa | (SEQ ID No:1) | 26,100 |
| 0.26 AIb | (SEQ ID No:2) | 20,500 |
| 0.19 AI  | (SEQ ID No:3) | 20,300 |
| 0.53 AI  | (SEQ ID No:4) | 3,940 |
| 0.28 AI  | (SEQ ID No:5) | 840 |

The numerical values as given herein for the amylase inhibitory activity are determined by the following method, which are represented in terms of the inhibitory activity value against human pancreatic α-amylase.

Determination of inhibitory activity against human pancreatic α-amylase:

An aqueous solution of a sample and human pancreatic α-amylase were added to 20 mM piperazine-N,N'-bis(2-ethanesulfonic acid) buffer (pH 6.9) containing 50 mM NaCl, 5 mM $CaCl_2$ and 0.02% egg white albumin. The mixture was allowed to stand at 37° C. for 30 min. and then mixed with 0.5 ml of a 1.5% soluble starch solution (pH 6.9). The resulting solution was allowed to react while maintaining at 37° C. for 10 min. and the reaction was then ceased by adding 2.5 ml of a solution (0.08M HCl and 0.4M acetic acid). To 0.2 ml of the reaction solution was added 2.5 ml of an iodine solution (0.05% KI and 0.005% iodine), and the mixture was measured for absorbance at 660 nm. The amylase was used in an amount sufficient to reduce 80% absorbance when no sample solution was contained and the amount of the amylase inhibitor sufficient to inhibit 50% amylase activity at this time was expressed as 1 amylase inhibitory unit (U).

The agents for inhibiting the accumulation of visceral fat may comprise one or more than one of the amylase inhibitors of wheat origin. For example, the agents may comprise as an active ingredient, an amylase inhibitor, only one of the proteins 0.26 AIa, 0.26 AIb and 0.19 AI, two of them or three (all) of them. Alternatively, the present agents may comprise a higher proportion of at least one of the proteins 0.26 AIa, 0.26 AIb and 0.19 AI and a lower proportion of the protein 0.58 AI, 0.28 AI, etc. which have a less amylase inhibitory activity.

In general, for producing the amylase inhibitor of wheat origin with a better productivity on an industrial scale, it is convenient to produce a mixture (roughly purified product) of plural proteins (amylase inhibitors) including the proteins 0.26 AIa, 0.26 AIb, 0.19 AI and, in some cases, the proteins 0.58 AI, 0.28 AI, etc., rather than to purify the respective proteins (amylase inhibitors) 0.26 AIa, 0.26 AIb or 0.19 AI until they are obtained in higher purity. Even such a mixture (roughly purified product) may exhibit a satisfactory inhibiting effect on visceral fat accumulation if it may have a high amylase inhibitory activity. Accordingly, the agents for inhibiting an accumulation of visceral fat may include both cases wherein a highly purified protein 0.26 AIa, 0.26 AIb or 0.19 AI is used as an amylase inhibitor for an active ingredient and wherein a roughly purified product in the form of a mixture thereof is used as an amylase inhibitor. If an amylase inhibitor comprising the mixture (roughly purified product) of the plural proteins having an amylase inhibitory activity as mentioned above is used, the agents can be produced at lower cost.

As amylase inhibitor mixtures (roughly purified products) which can be effectively used in the agents for inhibiting the accumulation of visceral fat and comprise the proteins 0.26 AIa, 0.26 AIb, 0.19 AI and/or other proteins having an amylase inhibitory activity, the following mixtures are recited for example.

Examples of the amylase inhibitors (in the form of a mixture) which may be used in the present agents for inhibiting the accumulation of visceral fat:

1. Amylase inhibitors produced by a process comprising the steps of:

(a1) extracting wheat, wheat flour or wheat gluten with water, a dilute acid, a dilute alkali or an aqueous alcohol to obtain a solution containing an amylase inhibitor;

(b1) adding a polysaccharide to said solution to form an insoluble complex of the amylase inhibitor with the polysaccharide and separating the insoluble complex from the solution;

(c1) separating the polysaccharide from the complex separated in the above step to collect a solution containing the amylase inhibitor; and (d1) treating the collected solution with a cation exchanger to recover the amylase inhibitor from the fractions that have not been adsorbed on the cation exchanger. This process is disclosed in Japanese Patent Kokai 5-301898.

2. Amylase inhibitors produced by a process comprising the steps of:

(a2) adding a polysaccharide to either an amylase inhibitor-containing solution extracted from wheat, wheat flour or wheat gluten with water, a dilute acid, a dilute alkali or an aqueous alcohol or an amylase inhibitor-containing waste water washings discharged during the recovery of starch and/or gluten from wheat flour, thereby forming an insoluble complex of the amylase inhibitor with the polysaccharide, and separating the insoluble complex from the solution;

(b2) separating the polysaccharide from the insoluble complex to collect an amylase inhibitor-containing solution;

(c2) precipitating 40–70% of the protein in the amylase inhibitor-containing solution to collect the protein thus precipitated and dissolving the collected protein in water to form an amylase inhibitor-containing solution;

(d2) adding a calcium ion and a phosphate ion to the solution obtained in the above step to form an insoluble complex containing the amylase inhibitor and separating the insoluble complex;

(e2) solubilizing the amylase inhibitor in water from the insoluble complex separated in the above step to form an amylase inhibitor-containing solution; and further including the step to remove impure proteins and other impurities at any stage up to the completion of the above step (c2). This process is disclosed in Japanese Patent Kokai 7-48268.

3. Amylase inhibitors produced by a process comprising the steps of:

(a3) treating an amylase inhibitor-containing solution extracted from wheat, wheat flour or wheat gluten with water, a dilute acid, a dilute alkali or an aqueous alcohol, or treating an amylase inhibitor-containing waste water washings discharged during the recovery of starch and/or gluten from wheat flour to modify soluble impure proteins and other impurities contained therein to their insoluble solid forms, and subsequently separating and removing the solid forms;

(b3) forming an insoluble calcium phosphate gel in the solution obtained in the above step (a3) while adsorbing the amylase inhibitor in said solution on said calcium phosphate gel, and subsequently separating and recovering the calcium phosphate gel containing the amylase inhibitor adsorbed thereon;

(c3) solubilizing the amylase inhibitor in water from the insoluble calcium phosphate gel obtained in the above step (b3) to form a solution containing the amylase inhibitor; and (d3) recovering the amylase inhibitor from the solution obtained in the above step (c3). This process is disclosed in Japanese Patent Kokai 7-48400.

The aforementioned protein 0.26 AIb which can be used in the agents for inhibiting an accumulation of visceral fat is a new amylase inhibitor. This 0.26 AIb can be prepared, for example, by subjecting the amylase inhibitors 1–3 as mentioned above (amylase inhibitors comprising a mixture of plural proteins having an amylase inhibitory activity; i.e., a roughly purified product) to high performance liquid chromatography by which a high pressure linear gradient elution with a time/concentration gradient is conducted by using, for example, a 0.1% aqueous solution of trifluoroacetic acid as Solution A and 80% acetonitrile and a 0.1% aqueous solution of trifluoroacetic acid as Solution B to fractionate the respective amylase inhibitors (proteins) by the differences in the retention time, and then recovering the fraction corresponding to the protein 0.26 AIb.

More specifically, following the steps (1)–(4) as described later in Reference Example 1, the dry powder (1 g) obtained in step (4) is dissolved in 100 ml of a 0.1% aqueous solution of trifluoroacetic acid and fractionated by a high performance liquid chromatography under the operating conditions shown in the following Table 2, whereby the 0.26 AIb can be separated and recovered.

TABLE 2

Operating Conditions for
High Performance Liquid Chromatography

Column:

Packing material: CAPCELL PAK C18 SG 120Å (particle size 3 μm) (manufactured by Shiseido Company, Limited)
Size: 4.6 mmϕ × 150 mm
Temperature: 50° C.

TABLE 2-continued

Operating Conditions for
High Performance Liquid Chromatography

Flow rate: 0.5 ml/min.
Detection: Absorbance at 280 nm
Mobile phase:

High pressure linear gradient elution with a
time/concentration gradient shown below, using
Solution A:  0.1% aqueous solution of trifluoroacetic
acid, and
Solution B:  80% aqueous solution of acetonitrile and 0.1%
aqueous solution of trifluoroacetic acid

| Time (min.) | Solution A (%) | Solution B (%) |
| --- | --- | --- |
| 0 | 65.5 | 34.5 |
| 30 | 65.5 | 34.5 |
| 60 | 64.5 | 35.5 |
| 60.1 | 0 | 100 |
| 65.0 | 0 | 100 |

Preferably, the agents for inhibiting the accumulation of visceral fat may contain an amylase inhibitor of wheat origin at a rate of 2,000–30,000 units (U) of an amylase inhibitory activity value per 1 mg of the agent, in order to exert an inhibiting effect on the accumulation of visceral fat. When said amylase inhibitor is composed of a mixture of plural amylase inhibitors having an amylase inhibitory activity, the above units are expressed as the sum of all amylase inhibitors.

The agents for inhibiting an accumulation of visceral fat may be composed of the aforementioned amylase inhibitor alone or in combination with other components derived from wheat such as proteins, peptides or other materials, e.g., starch, dietary fibers, vitamins, minerals.

The agents for inhibiting the accumulation of visceral fat may be ingested as such or may be applied in the form of a liquid preparation such as solutions, or a solid preparation such as granules or tablets formulated using conventional carriers or adjuvants for pharmaceutical preparation. Alternatively, the agents may be added to foods, in particular, carbohydrate foods rich in starch such as breads, cookies, noodles, etc., or tea, soup, seasoned fish meal, spreads such as butter or jam. In case where the agents are added to foods, care is needed so as not to lose the amylase inhibitory activity, since the amylase inhibitors of wheat origin frequently tend to lose or diminish their amylase inhibitory activity when heated to an elevated temperature, usually above 100° C. Further, it is preferable to control an amount of the agent to 100 mg–10 g per one meal.

This invention is further illustrated by the following examples.

REFERENCE EXAMPLE 1

Preparation of amylase inhibitor

To 800 kg of wheat flour were added 400 lit. of water and the mixture was kneaded to form a dough. The dough was washed with 6,000 lit. of water to recover 400 kg of gluten and 500 kg of wheat starch. At this stage, 5780 lit. of waste water washings were produced. The pH of waste water washings (aqueous extract) was adjusted to 3 with hydrochloric acid and after allowing to stand for 30 min., adjusted to pH 6.5 with aqueous ammonia, whereby insoluble matters were precipitated. The precipitates were removed to recover 4850 lit. of a supernatant.

To 1,000 lit. of the supernatant recovered as above were added 300 ppm of sodium alginate. The mixture was adjusted to pH 4.0 and 40 lit. of the gel thus formed were recovered. To the recovered gel was added calcium chloride (dihydrate) so as to give a calcium concentration of 400 ppm, thoroughly stirred and allowed to stand for one hour. Then, the gel was centrifuged by a De Laval centrifuge to recover about 10 lit. of the precipitate. To the precipitate were further added 30 lit. of water to wash the precipitate which was then centrifuged again by a De Laval centrifuge to give 6.5 kg of the precipitate. To the precipitate were added 25 lit. of water and then calcium chloride (dihydrate) so as to give a calcium concentration of 3,000 ppm. The mixture was thoroughly stirred and 25 lit. of the supernatant were recovered by a De Laval centrifuge. On the other hand, 5 lit. of the precipitate separated by a centrifuge were again washed with 12 lit. of an aqueous solution of calcium chloride (3,000 ppm) and the washings were recovered by a De Laval centrifuge. The washings were combined with 25 lit. of the supernatant as obtained previously to give 39 lit. of the eluate.

To 39 lit. of the resultant eluate were added 29.1 g of disodium hydrogenphosphate to adjust pH to 7.2. The resultant solution was heated to 80° C., thermally unstable material was removed by a De Laval centrifuge and the supernatant was concentrated by an ultrafiltration membrane ("NTU-3250 CIR" manufactured by Nitto Denko K.K.), while removing excess calcium salt to give a concentrated solution.

14 lit. of the resultant concentrated solution were adjusted to pH 7.5 with ammonia. After removing impurities by a filter press, the solution was treated with 3 kg of a cation exchange resin ("Diaion HPK-55" manufactured by Mitsubishi Kasei K.K.), and then adjusted to pH 4 with citric acid. The pH-adjusted solution was heat-treated at 80° C. and freeze-dried using freeze-dryer to give about 250 g of dry powders.

The dry powders were determined for the amylase inhibitory activity according to the aforementioned method to show the activity of about 8,000 U/mg. Those dry powders were used as an amylase inhibitor (an agent for inhibiting an accumulation of visceral fat).

The dry powders were fractionated by a high performance liquid chromatography under the operating conditions shown in Table 2 to investigate the sort of the proteins contained in the fractions, by which a chart shown in FIG. 1 was obtained. It was found that the dry powders contained the aforementioned proteins 0.26 AIa, 0.26 AIb, 0.19 AI, 0.53 AI, 0.28 AI, etc. In FIG. 1, the fraction at peak No. 10 was 0.19 AI, the fraction at peak No. 12 was 0.26 AIb, the fraction at peak No. 13 was 0.26 AIa, the fraction at peak No. 14 was 0.53 AI, and the fraction at peak No. 17 was 0.28 AI.

EXAMPLE 1

16 Wistar-strain male rats aged 6 weeks were divided into two groups, each consisting of 8 animals, and average body weight was measured.

The rats of the first group (Test group) were fed ad lib. over 2 weeks with a feed prepared by adding the dry powder product (an agent for inhibiting the accumulation of visceral fat) obtained in Reference Example 1, to the basal synthetic feed as shown in the following Table 3 at a rate of 2.4% based on the feed weight.

On the other hand, the rats of the second group (Control group) were fed ad lib. over 2 weeks with a feed prepared by adding an inactivated agent to the basal feed as shown in the following Table 3 at a rate of 2.4% based on the feed weight. The inactivated agent had been previously prepared by dissolving 400 g of dry powders (an agent for inhibiting the accumulation of visceral fat) obtained in Reference Example 1, in 2,000 ml of hot water (60° C.); adjusting the pH of the solution to 9.2; heating at above 90° C. for 10 min. to completely inactivate the amylase inhibitory activity followed by freeze-drying and pulverizing to powders.

TABLE 3

| Formulation of basal synthetic feed (parts by weight) | |
| --- | --- |
| α-Corn starch | 55 |
| Casein | 20 |
| Lard | 13 |
| Corn oil | 2.0 |
| Cellulose | 5.0 |
| Mineral mix | 3.5 |
| Vitamin mix | 1.0 |
| DL-Methionine | 0.3 |
| Choline bitartrate | 0.2 |
| Total | 100 |

After 2 weeks, rats of both groups were sacrificed and the liver, epididymal adipose tissue and mesenteric adipose tissue were collected. The weights of them were measured and an average value per one animal was calculated to obtain the results as shown in the following Table 4.

Then, the cytoplasmic fractions were prepared from the epididymal adipose tissue collected as above and the lipogenic enzymes contained in the fraction (fatty acid synthetase, malate dehydrogenase and glucose-6-phosphate dehydrogenase) were assayed for their enzymatic activity and an average value for the measurements of 8 rats was calculated to give the results as shown in the following Table 4.

Assay for activity of fatty acid synthetase in cytoplasmic fraction of epididymal adipose tissue:

The preparation of an enzyme solution and the assay for an enzymatic activity were performed according to the method by Muto & Gibson (Biochem. Biophys. Res. Commu., Vol. 38, pp. 9–15 (1970)), and the enzymatic activity of fatty acid synthetase (FAS), malate dehydrogenase (ME) and glucose-6-phosphate dehydrogenase (G6PDH) in the adipose tissue was assayed.

(i) Preparation of enzyme solution:

To 0.5 g of the rat epididymal adipose tissue was added 1 ml of 0.1M phosphate buffer (pH 7.4) containing 0.25M sucrose, 0.07M potassium hydrogencarbonate and 1 mM ethylenediaminetetraacetic acid disodium (EDTA-Na2) and 1 mM dithiothreitol (DTT), and the tissue was homogenized under ice-cooling by a Teflon homogenizer. The homogenized solution was centrifuged at 8,000×g at 4° C. for 20 min. to remove a mitochondrial fraction. The supernatant thus obtained was further centrifuged at 105,000×g at 4° C. for 60 min. by an ultra-high speed centrifuge and the supernatant fraction was used as an enzyme solution.

The assay of the FAS activity was carried out on the same day during which the enzyme solution was prepared. A portion of the supernatant fraction (the enzyme solution) obtained as above was frozen at −70° C. and the ME and G6PDH activities were assayed within two days after freezing according to the following methods.

(ii) Assay of FAS:

In a cuvette were incorporated in turn 20 µl of 12 mM NADPH (final concentration: 300 µM), 20 µl of 7 mM acetyl CoA (final concentration: 176 µM), 700 µl of a cocktail solution (0.114M L-histidine hydrochloride buffer; pH 6, containing 5.7 mM DTT and 4.57 mM EDTA-Na2)(final concentrations: histidine 100 mM, DTT 5 mM, EDTA 4 mM) and 40 µl of the enzyme solution as the enzymatic reaction solution and then the resulting mixture was stirred well. Immediately thereafter, the mixture was preincubated in an autographic spectrophotometer ("UV265-FS" manufactured by Shimadzu Corporation) set at 37° C. for 2 min., 20 µl of 3.2 mM malonyl CoA (final concentration of 78 µM) was added for reaction and a decreased rate of absorbance at 340 nm during the reaction was measured. The activity value of FAS was calculated from the amount of NADPH consumed during the reaction with a molar extinction coefficient of NADPH being defined as 6230.

(iii) Assay of ME activity:

In a cuvette were incorporated in turn 80 µl of distilled water, 40 µl of 0.1M magnesium chloride (final concentration: 4 mM), 20 µl of 12 mM β-NADP (final concentration: 0.24 mM), 800 µl of a cocktail solution (0.125M tris-hydrochloride buffer; pH 7.4, containing 0.125 mM DTT) (final concentrations: 0.1M Tris and 0.1 mM DTT) and 40 µl of the enzyme solution optionally diluted to 2–5 times with the said cocktail solution as the enzymatic reaction solution and then the resulting mixture was stirred well. Immediately thereafter, the mixture was preincubated in an autographic spectrophotometer ("UV265-FS" manufactured by Shimadzu Corporation) set at 37° C. for 2 min., 20 µl of 0.15M L-sodium malate (final concentration; 3 µM) was added for reaction and an increased rate of absorbance at 340 nm during the reaction was measured. The activity value of ME was determined from the amount of NADPH produced during the reaction.

(iv) Assay of G6PDH activity:

In a cuvette were incorporated in turn 100 µl of distilled water, 40 µl of 12 mM β-NADP (final concentration: 0.48 mM), 800 µl of a cocktail solution (0.125M tris-hydrochloride buffer; pH 8.0, containing 17.5 mM $MgCl_2$) (final concentrations: 0.1M Tris and 0.1 mM DTT) and 20 µl of the enzyme solution optionally diluted to 2–5 times with the said cocktail solution as the enzymatic reaction solution and then the resulting mixture was stirred well. Immediately thereafter, the mixture was preincubated in an autographic spectrophotometer ("UV265-FS" manufactured by Shimadzu Corporation) set at 37° C. for 2 min., 20 µl of 20 mM glucose-6-phosphate (final concentration: 0.8 mM) was added and reacted and then an increased rate of absorbance at 340 nm during the reaction was measured. The activity value of G6PDH was determined from the amount of NADPH produced during the reaction.

(v) Description of enzymatic activity:

The activity of fatty acid synthetase was expressed with the amount of NADPH consumed or produced in one min. by the enzyme per 1 mg of the protein in an enzyme solution, represented in terms of nmol (specific activity).

TABLE 4

| | First group (Test group) | Second group (Control group) |
| --- | --- | --- |
| Body weight (g/animal) | | |
| At the commencement of test | 117 ± 1 | 116 ± 1 |
| At the end of test (after 14 days) | 169 ± 1 | 169 ± 2 |
| Feed intake (g/14 days/2 animals) | 154 ± 2.4 | 157 ± 3.4 |
| Liver weight (g/animal) | 6.68 ± 0.11 | 6.59 ± 0.19 |
| Epididymal adipose tissue weight (g/animal) | 2.83 ± 0.05[2] | 3.06 ± 0.07 |
| Mesenteric adipose tissue weight (g/animal) | 2.26 ± 0.06[2] | 2.47 ± 0.07 |

TABLE 4-continued

|  | First group (Test group) | Second group (Control group) |
|---|---|---|
| Activity of lipogenic enzymes (nmol/min. · mg protein) | | |
| Fatty acid synthetase | 52.8 ± 3.7[1] | 67.6 ± 2.5 |
| Malate dehydrogenase | 392 ± 35[2] | 514 ± 28 |
| Glucose-6-phosphate dehydrogenase | 101.3 ± 7.5[2] | 125.9 ± 6.6 |

Footnote: All numerical values in Table 4 were expressed in terms of Mean ± S.E. (Standard Error)
[1] Significant difference at a significance level of 1% as compared with the control group
[2] Significant difference at a significance level of 5% as compared with the control group The results in Table 4 indicate that there is no substantial difference between the first group (Test group) and the second group (Control group) with regard to the body weight at the end of the test, feed intake and liver weight, and also that the epididymal adipose tissue weight and mesenteric adipose tissue weight were significantly lower in the first group (Test group) fed with the feed containing the present amylase inhibitor as compared with the second group (Control group) fed with the feed having no amylase inhibitory activity. This demonstrates that the present amylase inhibitors of wheat origin are effective for the inhibition of visceral fat accumulation.

Further, the results in Table 4 show that the activity of lipogenic enzymes in the adipose tissue was lower in the first group (Test group) fed with the feed containing the present amylase inhibitor as compared with the second group (Control group) fed with the feed having no amylase inhibitory activity. From such results, it was confirmed that the agents for inhibiting the accumulation of visceral fat of the present invention, which comprise an amylase inhibitor of wheat origin, can reduce the activity of lipogenic enzymes in the viscus thus inhibiting the accumulation of fat in the viscus.

Accordingly, the agents of the present invention which comprise as an active ingredient an amylase inhibitor of wheat origin, can suppress the accumulation of visceral fat in the viscus, thus preventing the visceral fat obesity which is said to be one of the causes of adult diseases. The present agents are applied safely because of their wheat origin, and can be taken conveniently without any physically incompatible feeling by oral administration or other routes as such or in the form of a food to which the agents are added.

What is claimed is:

1. A method for inhibiting accumulation of visceral fats, comprising: administering an effective amount of an amylase inhibitor of wheat origin.

2. The method of claim 1, wherein the amylase inhibitor contains at least one protein selected from the group consisting of a protein composed of two subunits, each identified as SEQ ID NO:1, a protein composed of two subunits, each identified as SEQ ID NO:2, and a protein composed of two subunits, each identified as SEQ ID NO:3.

3. The method of claim 1 wherein the concentration of amylase inhibitor is 2,000 to 30,000 units/mg.

4. The method of claim 1 wherein the amylase inhibitor is formulated into a liquid or solid preparation together with a pharmaceutically acceptable carrier or adjuvant.

5. An agent for inhibiting an accumulation of visceral fat which comprises as an active ingredient a protein composed of two subunits, each identified as SEQ ID NO:2.

6. A food additive comprising a protein composed of two subunits, each identified as SEQ ID NO:2.

* * * * *